United States Patent
Klepp et al.

(10) Patent No.: US 9,383,344 B2
(45) Date of Patent: Jul. 5, 2016

(54) LIQUID DISTRIBUTOR AND LIQUID COLLECTOR FOR CHROMATOGRAPHY COLUMNS

(75) Inventors: Georg-Heinrich Klepp, Bremen (DE); Sebastian Böcker, Leverkusen (DE); Jochen Strube, Hagen (DE); Heinz Kansy, Köln (DE); Hendrik Schmale, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 2191 days.

(21) Appl. No.: 11/574,849

(22) PCT Filed: Aug. 26, 2005

(86) PCT No.: PCT/EP2005/009229
§ 371 (c)(1),
(2), (4) Date: Jul. 13, 2007

(87) PCT Pub. No.: WO2006/027118
PCT Pub. Date: Mar. 16, 2006

(65) Prior Publication Data
US 2007/0246428 A1     Oct. 25, 2007

(30) Foreign Application Priority Data

Sep. 8, 2004   (DE) .......................... 10 2004 043 362

(51) Int. Cl.
| | | |
|---|---|---|
| *G01N 30/60* | (2006.01) | |
| *B01D 15/14* | (2006.01) | |
| *B01D 15/18* | (2006.01) | |
| *B01D 15/26* | (2006.01) | |
| *G01N 30/02* | (2006.01) | |

(52) U.S. Cl.
CPC ............ *G01N 30/6017* (2013.01); *B01D 15/14* (2013.01); *B01D 15/18* (2013.01); *G01N 30/02* (2013.01); *G01N 30/603* (2013.01); *G01N 30/6004* (2013.01); *Y10T 29/494* (2015.01)

(58) Field of Classification Search
CPC .............. G01N 30/6017; G01N 30/02; G01N 30/6004; G01N 30/603; Y10T 29/494; B01D 15/10; B01D 15/14; B01D 15/18
USPC ........................................ 210/656, 198.2, 456
See application file for complete search history.

(56) References Cited

U.S. PATENT DOCUMENTS

| | | | | |
|---|---|---|---|---|
| 4,354,932 A | * | 10/1982 | McNeil ...................... 210/198.2 |
| 4,450,082 A | * | 5/1984 | Tanouchi ............... B01D 15/00 |
| | | | | 210/290 |
| 4,537,217 A | * | 8/1985 | Allen, Jr. .................. 137/561 A |
| 4,636,315 A | * | 1/1987 | Allen, Jr. ............... B01D 15/14 |
| | | | | 210/198.2 |
| 4,891,133 A | | 1/1990 | Colvin | |

(Continued)

FOREIGN PATENT DOCUMENTS

| | | |
|---|---|---|
| DE | 411 8501 A1 | 12/1992 |
| JP | S 63-173960 A | 7/1988 |

(Continued)

*Primary Examiner* — Katherine Zalasky
(74) *Attorney, Agent, or Firm* — Norris McLaughlin & Marcus PA

(57) ABSTRACT

The present application relates to a liquid distributor and collector for columns for liquid chromatography with preferably round cross section, which is particularly suitable for columns with large diameter in relation to the packing height.

5 Claims, 1 Drawing Sheet

(56) References Cited

U.S. PATENT DOCUMENTS

| | | |
|---|---|---|
| 5,141,635 A | 8/1992 | LePlang et al. |
| 5,354,460 A | 10/1994 | Kearney et al. |
| 5,423,982 A | 6/1995 | Jungbauer et al. |
| 6,224,760 B1 | 5/2001 | Davies |
| 6,616,327 B1 * | 9/2003 | Kearney et al. ............... 366/340 |
| 6,742,924 B2 * | 6/2004 | Kearney ..................... 366/336 |
| 6,905,595 B2 * | 6/2005 | Gebauer .................... 210/198.2 |
| 2003/0024885 A1 * | 2/2003 | Ekholm ............... B01D 3/008 |
| | | 210/807 |
| 2004/0129641 A1 * | 7/2004 | Paananen ........... G01N 30/6017 |
| | | 210/656 |
| 2004/0140007 A1 | 7/2004 | Bellqvist |
| 2004/0140252 A1 * | 7/2004 | Gebauer ................ B01D 15/14 |
| | | 210/198.2 |
| 2005/0000879 A1 * | 1/2005 | Kearney et al. ............... 210/287 |

FOREIGN PATENT DOCUMENTS

| | | |
|---|---|---|
| JP | 2002-504015 A | 2/2002 |
| JP | 2002-507480 A | 3/2002 |
| JP | 2004-525384 A | 8/2004 |
| WO | WO89/11901 | 12/1989 |
| WO | WO 98/55198 | 12/1998 |
| WO | WO99/48599 | 9/1999 |
| WO | WO 02/093159 | 11/2002 |
| WO | WO 03/005018 | 1/2003 |

* cited by examiner

LIQUID DISTRIBUTOR AND LIQUID COLLECTOR FOR CHROMATOGRAPHY COLUMNS

This is a 371 of PCT/EP2005/009229 filed Aug. 26, 2005 (international filing date).

The present application relates to a liquid distributor and collector for columns for liquid chromatography, which is suitable particularly for columns with large cross-sectional area in relation to the packing height.

BACKGROUND OF THE INVENTION

Liquid distributors and collectors are used in column chromatography in order to uniformly distribute and to collect the liquid over the flow cross section. This is a necessary prerequisite to achieve the desired separating performance.

In order to accommodate the amounts of adsorbent required for the purification of the ever greater feed volumes in a column, development in chromatography is in the direction of larger column diameters, since there is an upper limit in the column length owing to the pressure drop and a minimum residence or process time. In order still to enable good separating performances in these columns with large cross-sectional area in relation to the packing height, new types of liquid distributors and collectors are required for equal distribution.

Known liquid distributors and collectors have slot construction (WO 03/005018 A1, WO 02/093159 A2, WO 98/55198), in which the input and output is via a central opening, and a narrow slot between opening and packing is intended to ensure uniform distribution. With increasing flow cross section, the uniformity of the distribution decreases as a result of the different lengths of the flow path (from the opening to the middle and from the opening to the edge of the packing cross section). A further approach consists in distributing the liquid toward the packing and collecting it by means of several openings (WO89/11901, WO99/48599). Equal distribution is ideally achieved by virtue of the same volume flow rate corresponding to each opening and the same residence time to each flow path. In construction terms, this is achieved by the same length and the same flow resistances (pressure drops) for the flow channels. With an increasing number of openings (>32), it is no longer possible to fulfill all criteria at the same time. This results either in solutions with complex flow channel geometries or, on the other hand, geometries which ensure equal distribution only for a certain volume flow rate.

A proven principle for the distribution of liquid between a relatively large number of openings with increasing flow cross section envisages the use of branching flow channels based on symmetrical T-distributors (U.S. Pat. No. 4,537,217, WO 99/48599). As a result of the equal length and geometric similarity of the flow channels, this principle ensures the same flow resistance and hence equal volume flow rates and equal residence times. However, with increasing flow cross section, it is not possible for all abovementioned criteria with regard to flow to be satisfied simultaneously for all cross-sectional shapes; equal length of the flow channels and equal flow resistances with large flow cross sections are achievable only with square flow cross sections (U.S. Pat. No. 4,537,217), while the same distribution of volume flow rates between the openings through strictly geometric distribution (WO 99/48599) can be obtained only by complex three-dimensional flow channel arrangements.

A design of the liquid distributors and collectors for chromatography columns which have a large diameter in relation to packing height is to date unknown with regard to the residence time of the liquid in the flow channels.

Proceeding from the prior art, it is thus an object of the invention to provide a liquid distributor and collector which can be designed even for large flow cross sections and, through uniform distribution, ensures the prerequisite for good separating performance, is subject to no restrictions with regard to its shape and can be manufactured in a very simple manner.

SUMMARY OF THE INVENTION

This object is achieved by the inventive flow distributor and collector by using, in addition to flow channels with symmetrical T-distributor shape, i.e. with equal length and cross-sectional area in each case, flow channels with asymmetrical T-shapes, i.e. the lengths and the cross-sectional areas of the flow channels may be of different size. The arrangement and dimensions of the flow channels can be selected such that the same time is required for the flow from the inlet to all outlets and from all inlets to the outlet of the liquid distributor and collector.

The mass flow rates which are assigned to each opening as a result of the arrangement and dimensions of the flow channels should be substantially of equal size.

The use of the same flow time as a crucial criterion for the equal distribution of the liquid over the flow cross section makes available a liquid distributor and collector which has a large number of openings and hence can service large flow cross sections, can be manufactured in a simple manner in one plane and from one component, is not restricted in the shape of its cross section and can thus be circular in accordance with most chromatography columns and can be scaled to any diameter. This enables conversion from the laboratory scale to industrial production scales. Compared with conventional chromatography columns of the same geometry under the same operating conditions, the chromatography columns manufactured using the inventive liquid distributor and collector have the advantage of improved separation.

DETAILED DESCRIPTION

The uniform distribution of liquid over large flow cross sections is achieved in the case of the inventive liquid distributor and collector by a very large number of equidistant openings, 50 to 5000, preferably 200 to 800, more preferably 300 to 400 square millimeters of cross-sectional area of the column packing are assigned to one opening.

The inventive liquid distributor and collector is further characterized in that the connecting liquid passages (flow channels) are arranged in one plane, and the cross section may be as desired, preferably round or rectangular, more preferably circular.

The inventive liquid distributor and collector may be manufactured from metal, from glass or any suitable plastic (for example polycarbonate, polyester, polymethyl methacrylate), preferably from metal, more preferably from corrosion-resistant metal, most preferably from stainless steel. To produce the inventive liquid distributor and collector, the flow channels may be introduced by machining (for example drilling, milling) of the material, but the liquid distributor and collector can also be produced by casting (for example of glass or plastic).

The liquid distributor and collector may be composed of a plurality of appropriately processed parts (for example by welding, soldering, adhesive-bonding or by a screw connection), or even consist of a single workpiece.

In a particularly preferred process for producing the inventive liquid distributor and collector, a single workpiece of stainless steel is provided with the appropriate flow channels and openings by milling and drilling.

Arrangement and dimensions of the flow channels for the inventive liquid distributor and collector are determined as follows:

To determine the optimal flow cross-sectional area which can be assigned to one opening of the liquid distributor and collector, in the laboratory and/or on the pilot scale, one pulse is applied to several columns with different cross sections under otherwise identical conditions, and the chromatograms provided by a detector are evaluated with regard to retention time, number of stages, symmetry and peak resolution. From this series, the largest flow cross section with still satisfactory separating performance is selected as the optimal flow cross-sectional area.

The optimal number of required openings of the liquid collector and distributor follows from the quotient of the flow cross-sectional area of the column packing on the production scale and the optimal flow cross-sectional area determined in the laboratory.

The openings of the flow collector and distributor are arranged equidistantly over the flow cross section predefined by the column to be used on the production scale. The individual openings are connected to one another by flow channels which form a network of symmetrical T-distributors. Adjacent openings and channels are each connected by a channel. The position of the flow channels and the dimension (height and width) of the individual flow channels are adjusted in a first approximation on the basis of geometric considerations and previous data such that approximately the same residence time is assigned to the flow path to each opening, which results in regions with flow channel sections of the same length and same cross-sectional area and regions with flow channels of different length and/or cross-sectional area. In addition, the volume flow rates assigned to the individual openings should be very similar. This design for the residence time and the volume flow rate is effected, for example, with the aid of numerical flow simulation, but other approximation and simulation processes are also conceivable. For example, the residence times and volume flow rates can be determined in a first approximation on the basis of the mass and energy or momentum balances for one-dimensional flow along a flow path between individual selected flow cross sections. A computer-supported model of the liquid distributor and collector is established, and the residence times and volume flow rates are determined on the basis of a flow simulation. Variations in the model geometries can then determine the geometry of the liquid distributor and collector in such a way that the abovementioned conditions are satisfied. In general, several iteration cycles are necessary, appropriately at least 2.

The liquid distributors and collectors are then tested in tests, and improvements in the geometry are still possible in some cases. Analogously to the procedure on the laboratory or pilot scale, pulses are applied to the column. Retention times, number of stages, symmetries and peak resolutions are determined from the chromatogram and compared with the values from the laboratory or pilot scale. Color experiments, i.e. the progress of a colored liquid front in the distributor in the packing and in the collector are possible when the components are manufactured from a transparent material.

With a given number of openings the liquid distributor and collector, while retaining the original size ratios of the flow channels, can be scaled to any technically viable diameter. The dimensions determined for the flow channels for a given liquid distributor and collector, i.e. the distances of the openings from one another, and also the length, the height and the width of the flow channels, while retaining the basic geometric arrangement, are provided with a factor leading to the target parameter.

Restrictions in the construction and in the manufacture make possible smaller deviations from the theoretical distribution in practical performance.

The inventive liquid distributor and collector can be used for the production of any chromatography columns for liquid chromatography (LC), supercritical liquid chromatography (SLC) and high-pressure or high-performance chromatography (HPLC), preferably in chromatography columns with large diameter in comparison to the packing height, which can in turn be used in analytical and preparative chromatography and in process chromatography, in elution chromatography, adsorption (LSC) and displacement chromatography, in chiral chromatography, normal phase chromatography, reverse phase chromatography (RPC), ion exchange chromatography (IEC), ion pair chromatography (IPC), ion exclusion chromatography, gel permeation chromatography (GPC) or gel filtration chromatography (GFC) or size exclusion chromatography (SEC), hydrophobic interaction chromatography (HIC), hydroxyapatite chromatography, affinity chromatography, immobilized metal affinity chromatography (IMAC), and both in batch chromatography and in continuous processes such as annular chromatography and in simulated moving bed (SMB) chromatography. Preference is given to the use in preparative chromatography, more preferably in preparative chiral chromatography, normal phase chromatography, reverse phase chromatography (RPC), ion exchange chromatography (IEC), gel permeation chromatography (GPC), hydrophobic interaction chromatography (HIC), hydroxyapatite chromatography, affinity chromatography, immobilized metal affinity chromatography (IMAC), and both in batch chromatography and in continuous processes, and in this context most preferably in simulated moving bed (SMB) chromatography.

These columns and their use in analytical and preparative chromatography likewise form part of the subject-matter of the present invention.

The use of a frit, preferably made of metal, ceramic, plastic, glass, preferably made of sintered metal and metal fabric, more preferably as a multilayer metal fabric (nominal width 5 to 500 micrometers), also with coarse-pore drainable fabric (nominal width 0.5 to 5 mm), can further improve the equal distribution of the liquid distributor and collector.

The inventive liquid distributor and collector can also be used for other objectives which are used a uniform distribution of liquid over a certain number of openings on a surface on which, for example, vessels assigned to the openings may also be arranged. A conceivable use is for sample application, for example in high-throughput screening.

The invention is illustrated in detail below with reference to the figures but without restricting it thereto.

EXAMPLES

Figure 1:
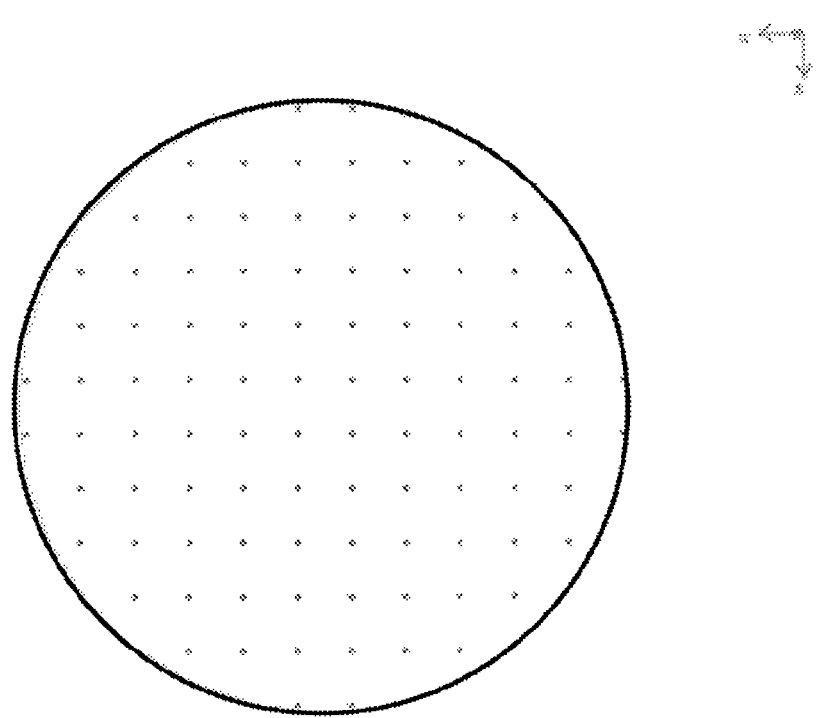
FIG. 1 the side of the liquid distributor and collector facing toward the column packing.

FIG. 1 shows the side of the liquid distributor and collector facing toward the column packing. 96 equidistant openings which are arranged uniformly over the circular flow cross section can be seen. The openings are circular.

Figure 2:
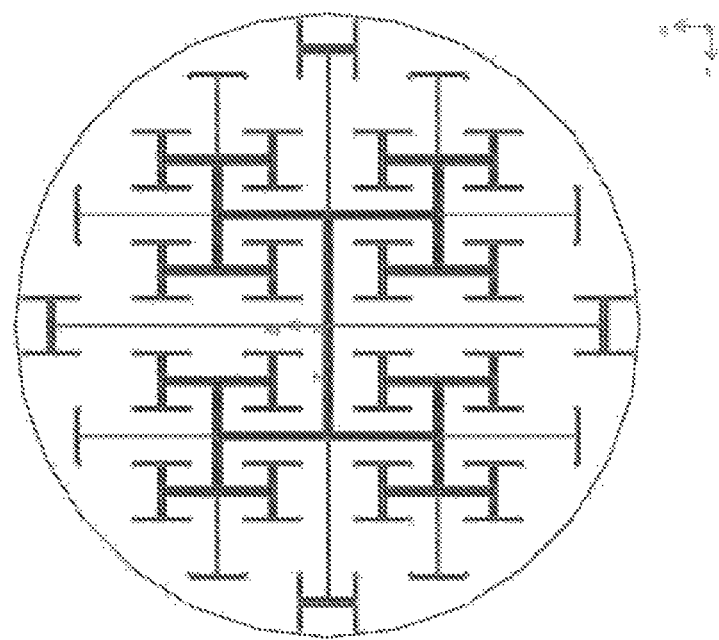
FIG. 2 the side of the liquid distributor and collector facing away from the column packing, with inlet and outlet, and flow channels.

FIG. 2 shows the side of the liquid distributor and collector facing away from the column packing, with inlet and outlet at the center. The flow channels are shown in symmetrical and asymmetrical T-distributor shape. The openings toward the column packing are each in the tips of the Ts.

The invention claimed is:

1. A round-shaped liquid distributor and liquid collector for chromatography columns, comprising at least one liquid inlet and outlet opening and connecting flow channels between the at least one inlet and outlet opening to equidistantly arranged openings to a column packing, wherein some of the connecting flow channels are of symmetrical T-distributor shape, the rest of asymmetrical T-shapes, and the same time is required for flow from the inlet to the outlet of the liquid distributor or collector through the different connecting flow channels, and the same length and the same cross-sectional area, and the connecting flow channels of asymmetrical T-distributor shape have a different length and a different cross-sectional area than the connecting flow channels of symmetrical T-distributor shape, and the cross section of the liquid distributor or collector is round.

2. The round-shaped liquid distributor and collector of claim 1, wherein one opening to the column packing is provided for each 50-5000 square millimeters of cross-sectional area of the column packing.

3. The round-shaped liquid distributor and collector as claimed in claim 1, wherein the connecting flow channels are arranged in one plane.

4. A chromatography column comprising the round-shaped liquid distributor and collector of claim 1.

5. A method for analytical and preparative chromatography which comprises conducting said analytical or preparative chromatography in a chromatographic column having a round-shaped liquid distributor and collector of claim 1.

* * * * *